(12) United States Patent
Hall et al.

(10) Patent No.: US 6,290,699 B1
(45) Date of Patent: Sep. 18, 2001

(54) ABLATION TOOL FOR FORMING LESIONS IN BODY TISSUE

(75) Inventors: Jeffrey A. Hall; David C. McGiffin, both of Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/348,811

(22) Filed: Jul. 7, 1999

(51) Int. Cl.$^7$ .................................................. A61B 18/14
(52) U.S. Cl. ........................... 606/41; 607/99; 607/105; 607/113; 607/119; 604/114
(58) Field of Search .................. 606/41; 607/99, 607/105, 113, 119, 122; 604/114

(56) References Cited

U.S. PATENT DOCUMENTS

| | | | |
|---|---|---|---|
| 5,582,609 | 12/1996 | Swanson et al. | 606/39 |
| 5,658,278 | 8/1997 | Imran et al. | 606/41 |
| 5,697,927 | 12/1997 | Imran et al. | 606/41 |
| 5,720,719 | 2/1998 | Edwards et al. | 604/22 |
| 5,743,904 | 4/1998 | Edwards | 606/32 |
| 5,792,140 | 8/1998 | Tu et al. | 606/41 |
| 5,849,028 | 12/1998 | Chen | 607/102 |
| 5,853,409 | 12/1998 | Swanson et al. | 606/31 |
| 5,857,977 | 1/1999 | Caswell et al. | 600/518 |
| 6,068,629 | * 5/2000 | Haissaguerre et al. | 606/41 |
| 6,071,281 | * 6/2000 | Burnside et al. | 606/41 |
| 6,106,522 | * 8/2000 | Fleischman et al. | 606/41 |

* cited by examiner

*Primary Examiner*—Lee Cohen
(74) *Attorney, Agent, or Firm*—Myers Bigel Sibley & Sajovec, P.A.

(57) ABSTRACT

The present tool and associated methods provide for precisely controlled positioning of an ablative element, or an array of ablative elements, against a tissue targeted for treatment. Such treatment is in the form of a lesion, caused by energy emitted from the ablative element, selectively changing or destroying cells within the target tissue. The tool incorporates an element array. This element array consists of one or more energy emitting (ablative) elements. The energy delivered may be in the form of radio frequency, microwave, ultrasound, light, and cryogenics, among others. The element array may also incorporate one or more temperature sensing elements. Further, this element array may incorporate a fluid system providing recirculative cooling or fluid delivery to cool the element array and/or surrounding tissue. In one use of the tool, the element array, which is located at the distal end of an elongate member, is positioned against cardiac tissue during an open heart procedure. The elongate member and the element array may be bent and formed to facilitate access and to produce the desired lesion shape.

32 Claims, 8 Drawing Sheets

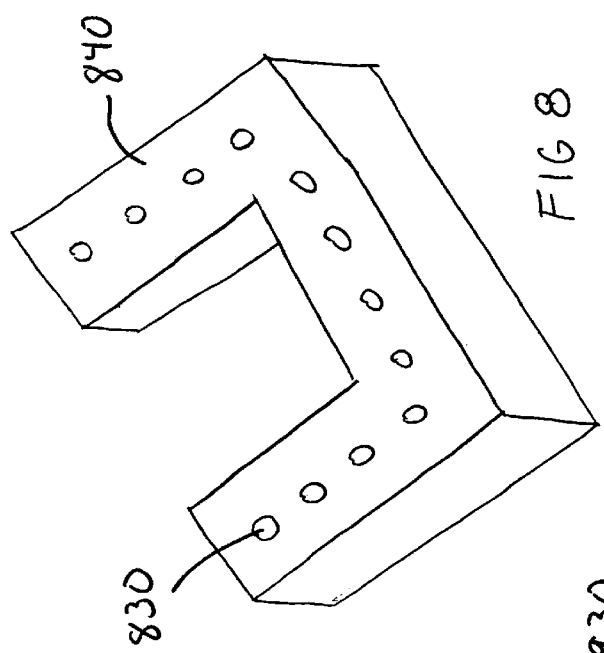
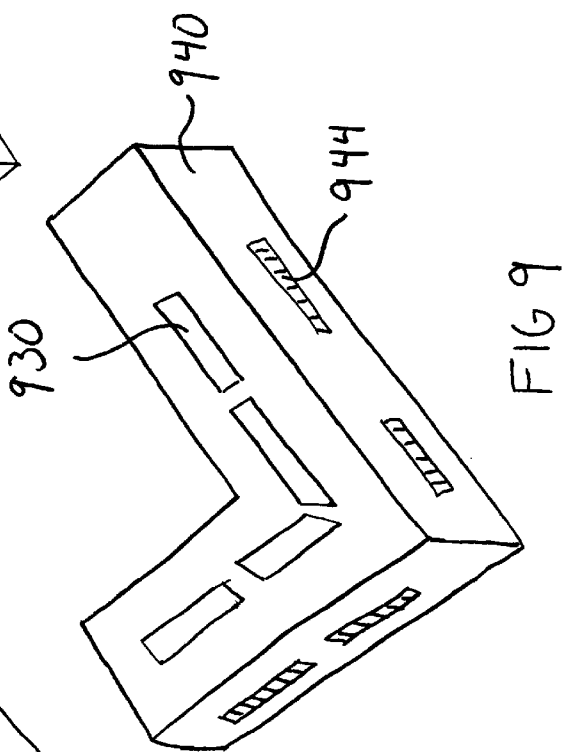
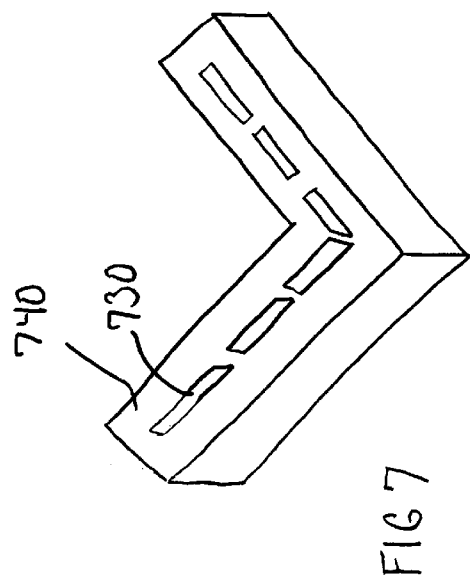

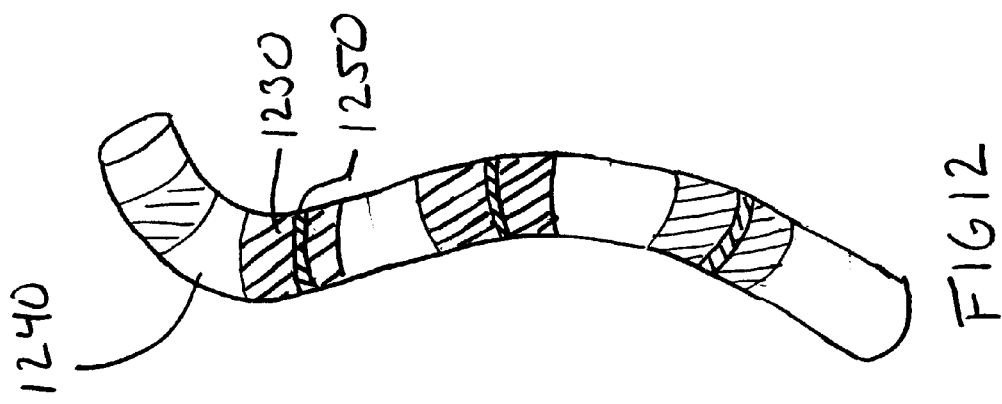
FIG 12
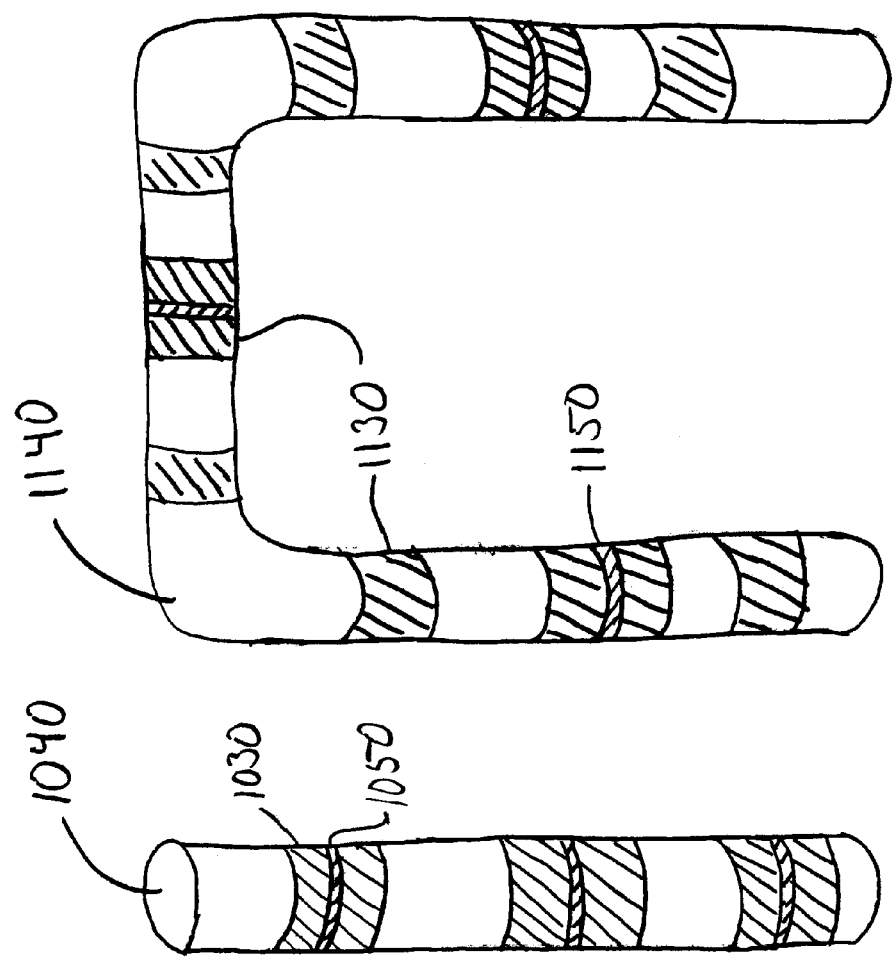
FIG 11
FIG 10

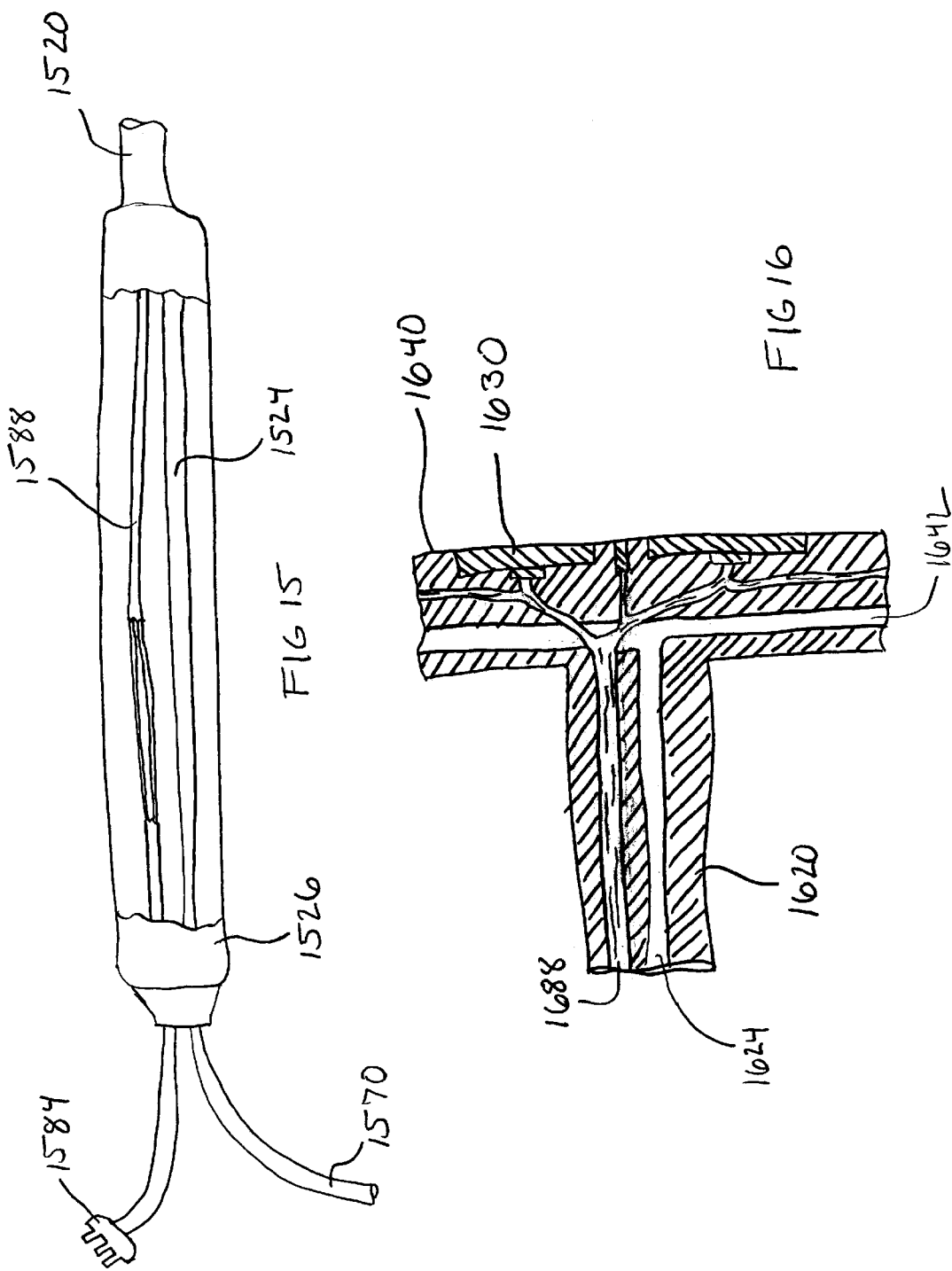

ABLATION TOOL FOR FORMING LESIONS IN BODY TISSUE

TECHNICAL FIELD

The present description generally relates to medical tools and methods, and more particularly, an ablation tool and methods of use for forming lesions in body tissue.

BACKGROUND

Physicians employ tissue ablation to treat various medical conditions, including cardiac rhythm disfunction and benign prostatic hypertrophy. Tissue ablation is the process of directing energy to the target tissue site to form a lesion. The energy delivered may be in the form of radio frequency, microwave, ultrasound, light energy, and cryogenics, among others. In the case of the treatment of cardiac disfunction, lesions of different shape and size have been used to treat atrial fibrillation and ventricular tachycardia, among others.

Percutaneous transluminal ablation (PTA) catheters are frequently used for cardiac tissue ablation. The PTA catheters are long, slender, and flexible such that they can be inserted through a small incision through the skin into a blood vessel, such as an artery or vein, and advanced to the treatment site. Once positioned, the PTA catheter is used to selectively ablate or "burn" selected tissue which results in a change in the physiology of the treatment site. Such treatments may be used to block electrical conduction to correct abnormal cardiac rhythm that interferes with proper organ function.

PTA catheters use any of a number of methods to deliver ablative energy to the tissue. Some of these methods utilize radio frequency and microwave. The energy delivery component of the PTA catheter, sometimes referred to as an ablating element or electrode, is located either at the distal tip or along a portion of the distal end of the PTA catheter. When the PTA catheter is advanced through the blood vessel to the treatment site, either the tip or the side of the PTA catheter, depending on electrode type, is pressed against the tissue to be ablated.

Creation of linear lesions in the right and left atrium results in a progressive increase in the organization of atrial activity until sinus rhythm is restored. M. Haissaguerre, et al., reported successful ablation of atrial fibrillation in a patient with paroxysmal atrial fibrillation by the creation of three linear lesions in the right atrium, two longitudinal and one transverse, that connected the two longitudinal lesions using a specially designed catheter (Haissaguerre M, Gencel L, Fischer B, Metayer P L, Poquet F, Marcus F I, Clementy J., Successful Catheter Ablation of Atrial Fibrillation, J Cardiovasc Electrophysiol 1994;5:1045–1052).

Successful ablation therapy is defined as a return to normal sinus rhythm. To achieve this, lesions need to be continuous, transmural, and connected with other lesions or anatomical structures that cause blockage of atrial conduction. The seven recommended lesions are as follows: 1) right atrial isthmus ablation: linear lesion applied to the right atrium between the tricuspid annulus and the eustachian ridge, 2) right atrial inter-caval ablation: linear lesion applied along the posterior wall of the right atrium, between the superior vena cava and the inferior vena cava, 3) right pulmonary vein ablation (RPV): linear lesion applied to the left atrium, beginning below Bachmann's bundle, across the right superior pulmonary vein (RSPV) to the right inferior pulmonary vein (RIPV) and adjoining the mitral annulus, 4) left pulmonary vein ablation (LPV): linear lesion applied to the left atrium, beginning below Bachmann's bundle, across the left superior pulmonary vein (LSPV) to the left inferior pulmonary vein (LIPV) and reaching the mitral annulus, 5) superior pulmonary vein ablation (SPV): linear lesion applied to the left atrium, across the right superior pulmonary vein to the left superior pulmonary vein, 6) left atrial roof ablation (ROOF): linear lesion applied from the trigone, across the roof of the left atrium, to the left superior pulmonary vein, and 7) left atrial septal ablation (SEP): linear lesion applied to the foramen ovale to the right superior pulmonary vein. During creation of the right atrial inter-caval line, pacing is performed from each pair of electrodes at high output to assure the absence of diaphragmatic stimulation.

PTA catheters are designed for and have been used successfully for transluminal use; that is, via minimally invasive surgery. There is a need to have the capability to apply ablation therapy non-transluminally, such as during open heart surgery. For example, some patients having surgery for the treatment of atrio-ventricular valve disease would benefit from ablation therapy in order to correct cardiac arrhythmias of the atria or ventricle. Up to 40% of patients requiring mitral valve replacement have concurrent atrial fibrillation (fast atrial arrhythmia) which can be treated by creation of long linear ablation lines in the atria. During the open heart procedure, the physician is presented with a direct view of the target tissue to which ablation therapy may be applied, negating the need to approach the site transluminally. PTA catheters are inadequate for use in the open heart procedure, as they lack the structural support required to direct and press the electrodes against the target site. Also, due to their need to traverse narrow, tortuous vasculature, there is a definite limitation as to electrode size, shape and configuration available from PTA catheters.

SUMMARY

In general, the present tool and associated methods provide for precisely controlled positioning of an ablative element, or an array of ablative elements, against a tissue targeted for treatment. Such treatment is in the form of a lesion, caused by energy emitted from the ablative element, selectively changing or destroying cells within the target tissue.

The present tool and associated methodology provides a precise, controlled medical treatment which is suitable for destroying cells of medically targeted tissues throughout the body, both within and external to body organs. The tool is particularly useful for treating cardiac disfunction, such as atrial fibrillation, and the tool and its use are hereinafter described with respect to cardiac treatment, for purposes of simplifying the description thereof. The direct visualization and exposure of the heart tissue as provided during open heart procedures allow for a more direct and simplified approach to ablation on either the endocardium or epicardium. The lesions produced may be similar to those provided by ablation catheters or may be very different, taking advantage of the accessibility provided by the open heart procedure. For example, the isolation of the pulmonary veins from the rest of the atria could be accomplished in a very different fashion with a direct sight ablation tool as compared with ablation catheter techniques. It will be readily apparent to a person skilled in the art that the tool can be used to change or destroy body tissues in any body cavity or tissue locations that are accessible by invasive surgery, and is not limited to the heart. Application of the tool in all of these organs and tissues is intended to be included within the scope of this invention.

One aspect of the tool and associated methodologies provides for creating lesions of complex shape and size. This provides the surgeon with the ability to create the necessary lesion pattern with one or a few applications of the tool, as opposed to the multiple and repetitious application required of percutaneous transluminal ablation (PTA) catheters used currently. The tool incorporates an element array. This element array consists of one or more energy emitting (ablative) elements. The energy delivered may be in the form of radio frequency, microwave, ultrasound, light energy, and cryogenics, among others. The element array may also incorporate one or more temperature sensing elements, such as thermocouples and thermistors. Further, this element array may incorporate a fluid system providing recirculative cooling or fluid delivery to cool the element array and/or surrounding tissue.

In one embodiment, the element array consists of a single energy emitting element located at the distal end of an elongate member. In another embodiment that implements this aspect of the tool, the energy emitting element incorporates a temperature sensing element. The energy emitting element may have the property of producing a point lesion or an elongated lesion, singularly or in combination. Such resulting elongated lesion may be straight, curved, or of an enclosed shape, such as a circle.

In one embodiment, the element array consists of multiple energy emitting elements located at the distal end of an elongate member. In another embodiment that implements this aspect of the tool, the energy emitting elements incorporate one or more temperature sensing elements, such as thermocouples or thermistors. Each energy emitting element may have the property of producing a point lesion or an elongated lesion, singularly or in combination. Such resulting elongated lesion may be straight, curved, or of an enclosed shape, such as a circle. The combination of element placement and element shape provides a tool capable of producing lesions of complex shape and size. In one embodiment that implements this aspect of the tool, the element array comprises a planar surface, wherein the energy emitting and temperature sensing elements are arranged on the planar surface. In one embodiment, the planar surface is elongated, such as to produce a lesion or series of lesions having a generally elongated shape. In another embodiment, the planar surface is more complex, forming an overall lesion shape in the general form of an "L", "U", or "V", among others shapes that provide lesions with the desired therapeutic shape and outcome.

In one embodiment, the elongate member has a rigid, preformed shape suitable for the particular intended use.

In another embodiment that comprises an element array consisting of one or more energy emitting elements located at the distal end of an elongate member, the element array is malleable, having the capability of being formed or shaped. The combination of element placement, element shape, and malleability provides a tool capable of producing lesions of complex shape and size, which can be custom shaped for the particular target site. The energy emitting and temperature sensing elements may be of the form of a disk, band, ribbon, wire, coil, among others.

In another embodiment that implements this aspect of the tool, the element array has a cylindrical configuration. The energy emitting and temperature sensing elements my be bands, rings, coils, disks, ribbon, wire, and the like. The cylindrical shape allows for forming or bending into complex shapes with minimal kinking, if made from a malleable material. Since the elements encircle the element array, direct target tissue sighting is not required; that is, tissue hidden from a direct line of sight can be targeted, such as the backside of a protrusion, lump or step.

When the ablation tool is used during an open heart cardiac procedure, the element array is positioned within the body, such that the energy emitting elements and temperature sensing elements are in a position to be urged against the target body tissue. While the element array is held against the tissue, energy is applied to the energy emitting elements while the temperature sensing elements collect and transmit temperature data to the user. In one embodiment, the element array is of a design to allow not only the pushing of the element array against the tissue, but also pulling, as in the case where the target tissue is behind an obstruction or protrusion. Since, in this embodiment, the energy emitting elements and the temperature sensing elements encircle the element array, the exact placement of the element array to contact the target tissue is less critical.

This summary is a brief overview of some embodiments of an ablation tool and methods of use and is not intended to be exclusive or limiting and the scope of the invention is provided by the attached claims and their equivalents.

BRIEF DESCRIPTION OF THE DRAWINGS

FIG. 7 is a perspective view of one embodiment of an element array of an ablation tool.

FIG. 8 is a perspective view of one embodiment of an element array of an ablation tool.

FIG. 9 is a perspective view of one embodiment of an element array of an ablation tool.

FIG. 10 is a perspective view of one embodiment of an element array of an ablation tool.

FIG. 11 is a perspective view of one embodiment of an element array of an ablation tool.

FIG. 12 is a perspective view of one embodiment of an element array of an ablation tool.

FIG. 15 is a cut-away view of one embodiment of a part of an ablation tool.

FIG. 16 is a cross-sectional view of one embodiment of a part of an ablation tool.

DETAILED DESCRIPTION

Figure 1:
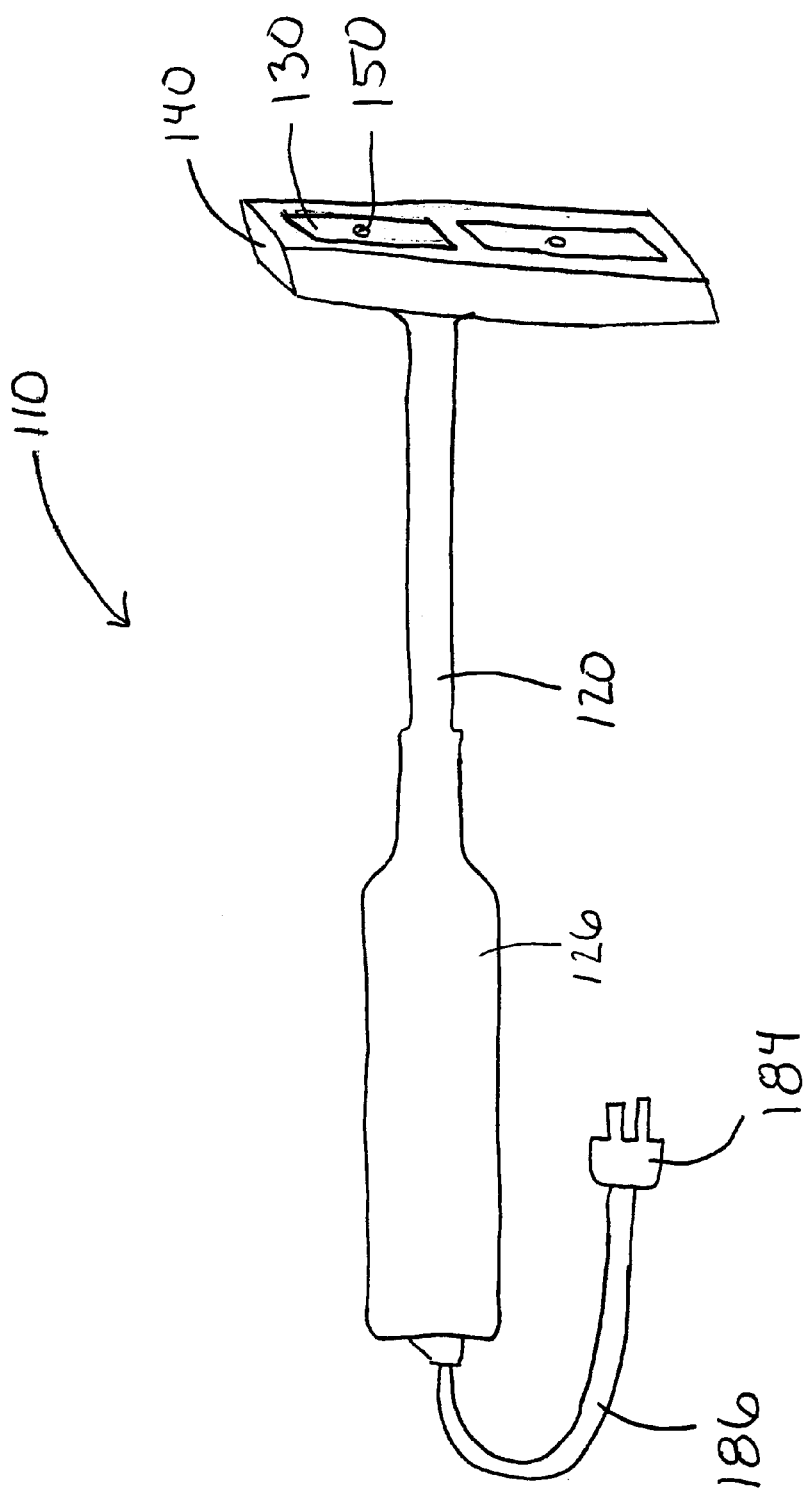
FIG. 1 is a perspective view of one embodiment of an ablation tool.

In the following detailed description, reference is made to the accompanying drawings, which are not necessarily to scale, which form a part hereof, and in which is shown by way of illustrating specific embodiments in which the device may be practiced. These embodiments are described in sufficient detail to enable those skilled in the art to practice the device, and it is to be understood that the embodiments may be combined, or that other embodiments may be utilized and that structural changes may be made without departing from the spirit and scope. The following detailed description is, therefore, not to be taken in a limiting sense, and the scope is defined by the appended claims and their equivalents. In the drawings, like numerals describe substantially similar components throughout the several views.

The present apparatus and methods will be described in applications involving cardiac ablation. However, it is understood that the present apparatus and methods may be employed in other tissue ablation applications.

FIG. 1 shows an embodiment of an ablation tool 110 for making lesions in body tissue. The ablation tool 110 has an elongate member 120 having an element array 140 at one end and a handle 126 and associated cabling 186 terminating in a cable plug 184. A plurality of energy emitting elements 130 and temperature sensing elements 150 are disposed on the element array 140. The energy emitting elements 130 and temperature sensing elements 150 are embedded within the element array 140 and flush with the surface of the element array 140. When the ablation tool 110 is in use during an open heart cardiac procedure, the element array 140 is positioned within the body, such that the energy emitting elements 130 and temperature sensing elements 150 are in contact with the body tissue. Energy is applied to the energy emitting elements 130 while the temperature sensing elements 150 collect and transmit temperature data to the user.

In one embodiment, elongate member 120 may be made of a rigid material. The elongate member 120 may be straight or curved depending on the application and use. In another embodiment, the elongate member 120 may be malleable to permit bending to a preferred configuration and yet retain enough rigidity to resist gross deformation when the element array 140 is urged against body tissue. In one embodiment, the elongate member 120 is made of a flexible material having embedded within a malleable wire. In another embodiment, the elongate member 120 is made of a malleable metal, such as nickel-titanium, which may be bent and retain its shape once bent.

Figure 2:
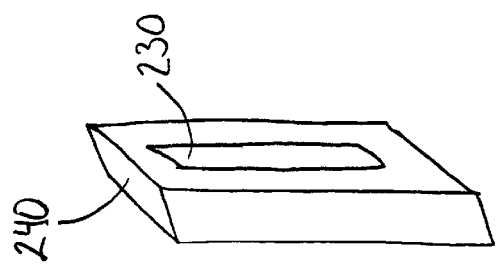
FIG. 2 is a perspective view of one embodiment of an element array of an ablation tool.

FIG. 2 shows an embodiment of an element array 240 and an energy emitting element 230 embedded within. Energy emitting element 230 may be of any shape, such as circular or rectangular, depending on the intended use. A single energy emitting element 230 may be used to make relatively small lesions, or with the repetitive use of the tool, produce a larger lesion in a continuous or discontinuous configuration.

Figure 3:
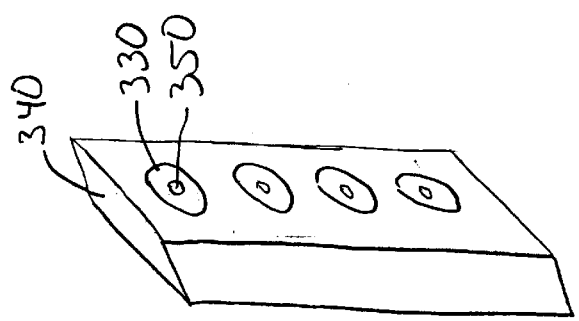
FIG. 3 is a perspective view of one embodiment of an element array of an ablation tool.

FIG. 3 shows another embodiment wherein the element array 340 contains a plurality of energy emitting elements 330 and temperature sensing elements 350. The placement and number of energy emitting elements 330 and temperature sensing elements 350 depend on the intended use. For producing small lesions a fewer number of energy emitting elements 330 and temperature sensing elements 350 are used. For producing large lesions of complex shape, a larger number of energy emitting elements 330 and temperature sensing elements 350 are used.

Figure 4:
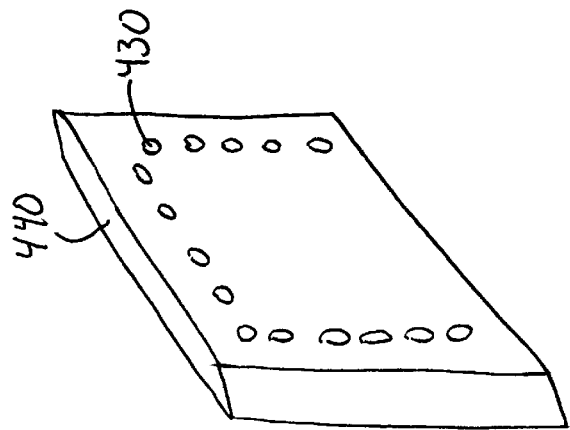
FIG. 4 is a perspective view of one embodiment of an element array of an ablation tool.

FIG. 4 shows an embodiment of an element array 440 with energy emitting elements 430 configured is a generalized "U" pattern. Such a configuration may produce a lesion that is segmented or continuous depending on the type, intensity, and duration of the applied energy. Such a complex configuration may allow the physician to make the required therapeutic lesion in the body tissue with one application of the tool. This would minimize procedure time and complexity.

Figure 5:
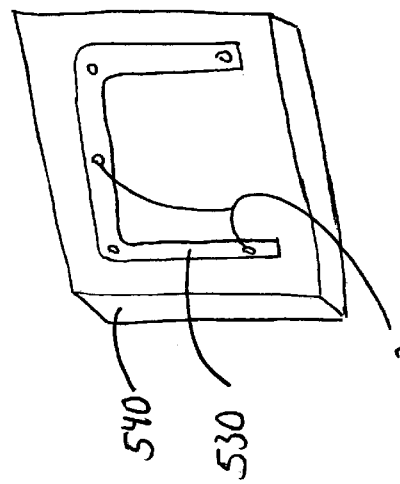
FIG. 5 is a perspective view of one embodiment of an element array of an ablation tool.

FIG. 5 shows another embodiment of an element array 540 in combination with a single but complex shaped energy emitting element 530 and a temperature sensing element 550. In this embodiment, a larger, more complex continuous lesion may be made with lower energy and less duration than an element array with multiple discontinuous energy emitting elements 430 as shown in FIG. 4. Temperature sensing element 550 allows for monitoring the applied temperature by the energy emitting element 530.

Figure 6:
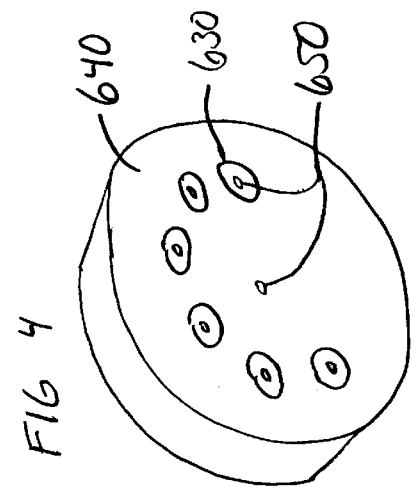
FIG. 6 is a perspective view of one embodiment of an element array of an ablation tool.

FIG. 6 shows another embodiment of the element array 640 which is of a circular shape. The energy emitting elements 630 are in a generally curved or circular configuration and temperature sensing element 650 is placed for monitoring temperature.

FIG. 7 shows an embodiment of an element array 740 that is generally shaped as the letter "L" or "V". Such a configuration provides a lesion shape that may be obtained in one use of the tool, whereas with an array of another shape may require multiple uses. FIG. 8 shows another embodiment of an element array 840 that is generally shaped as the letter "U". Lesions of this shape are commonly needed in the treatment of cardiac conditions. FIG. 9 shows an embodiment of an element array 940 incorporating fluid orifices 944. Fluid orifices 944, when connected to a fluid source, provides for the drenching of the tissue surrounding the target tissue to minimize collateral heating of the surrounding tissue.

FIGS. 10, 11, and 12 show other embodiments of the element array 1040, 1140, and 1240, respectively. In general, element arrays 1040, 1140 and 1240 are of a rod or cylindrical shape. The energy emitting elements 1030, 1130, and 1230, and the temperature sensing elements 1050, 1150, and 1250 may have the configuration of a band, coil, or disk. Such a configuration allows the tool to be used in a number of different ways not available with the planar or flat faced configurations such as those in FIGS. 1–9. The element arrays of FIGS. 10–12 allows not only the pushing of the element array 1040, 1140 and 1240 against the tissue, but also pulling, as in the case where the target tissue is behind an obstruction or protrusion. Since the energy emitting elements 1030, 1130, and 1230 and the temperature sensing elements 1050, 1150, and 1250 encircle the element array 1040, 1140, and 1240, the exact placement of the element array to contact the target tissue is less critical.

The element arrays shown in FIGS. 10–12 may be rigid and formed in a predetermined shape, or may be malleable, such that they may be bent and formed as the application requires. The cylindrical shape of the element array 1040, 1140 and 1240 allows for bending with less chance of kinking as may occur with other configurations.

Figure 13:
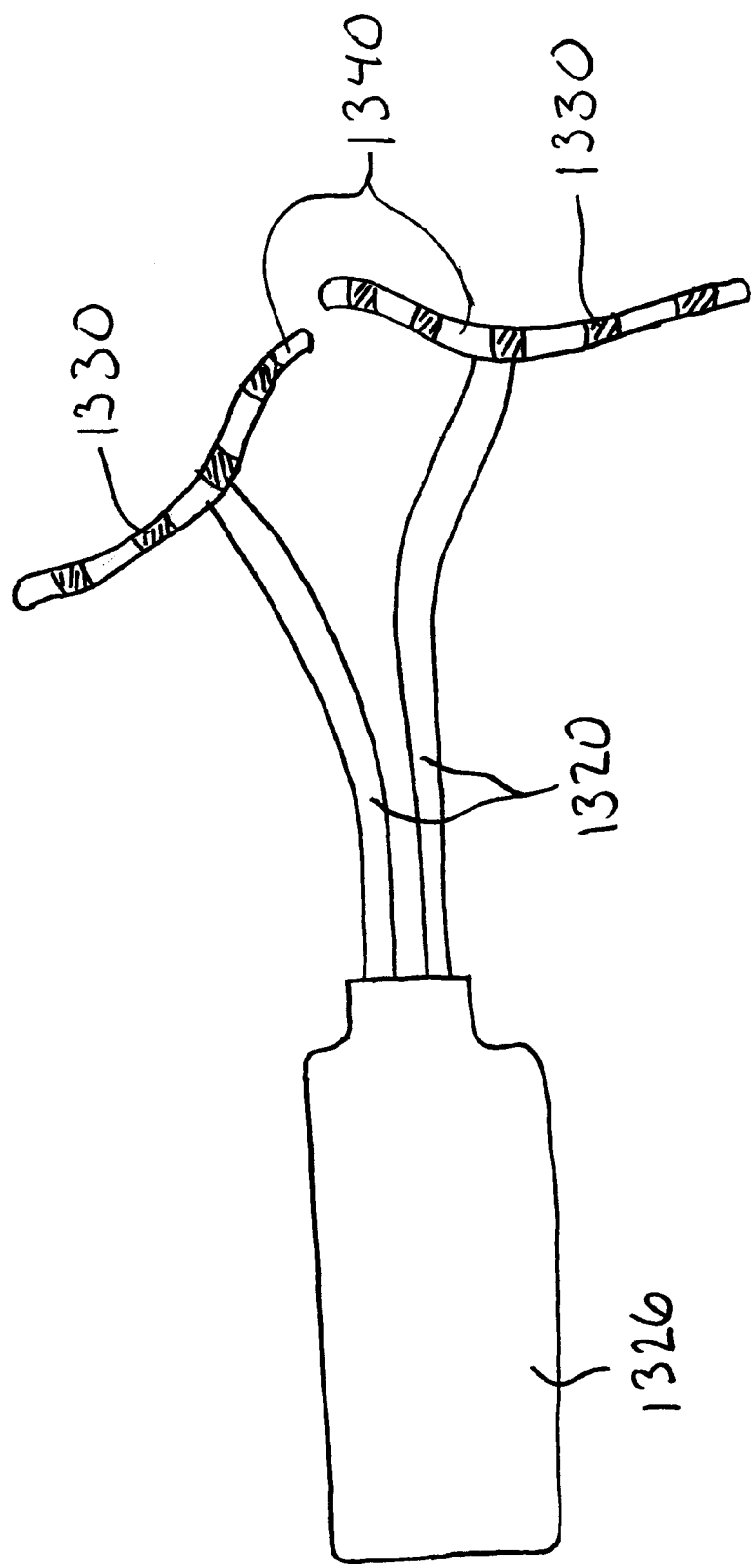
FIG. 13 is a perspective view of one embodiment of an ablation tool.
Figure 14:
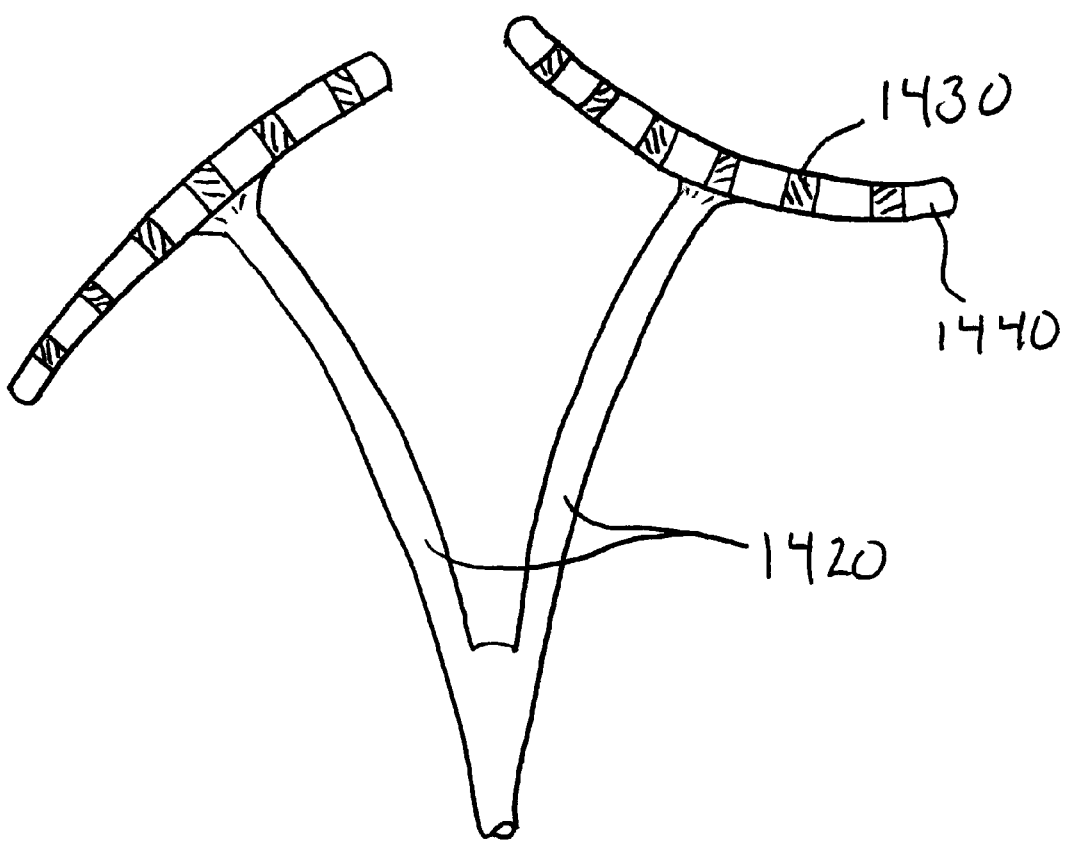
FIG. 14 is a perspective view of one embodiment of a section of an ablation tool.

FIG. 13 shows an embodiment of an ablation tool having a handle 1326, and two elongate members 1320, each having an element array 1340 with corresponding energy emitting elements 1330. The two elongate members 1320 are made from a malleable material such that they may be bent and formed into a desired, complimentary configuration such that the two element arrays 1340 may contact the tissue simultaneously in a desired shape and location. In another embodiment, element arrays 1340 are malleable such that they may be bent and formed in a complex shape as required. Such a system provides for uses not obtainable from systems with one element array 1340. FIG. 14 shows another embodiment with multiple elongate members 1420 that are joined at their respective proximal ends.

FIG. 15 shows a cut-away view of an embodiment of an ablation tool handle 1526 incorporating a lumen 1524 which provides for the passage of fluid from a fluid source 1570 to the element array lumen 1644 shown in FIG. 16, and orifice 944 shown in FIG. 9. FIG. 16 shows a cross-section of an embodiment of a portion of an elongate member 1620 and the element array 1640. The elongate member fluid lumen 1624 is in fluid communication with the element array 1640 fluid lumen.

Figure 17A:
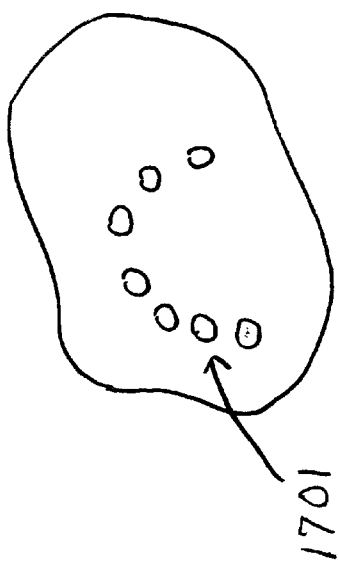
FIG. 17A is a top view of a lesion pattern.
Figure 17B:
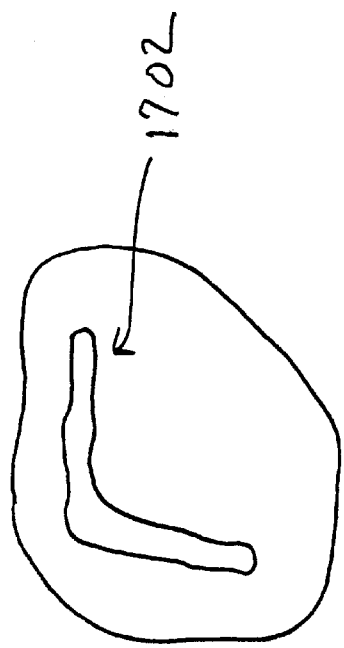
FIG. 17B is a top view of a lesion pattern.
Figure 17C:
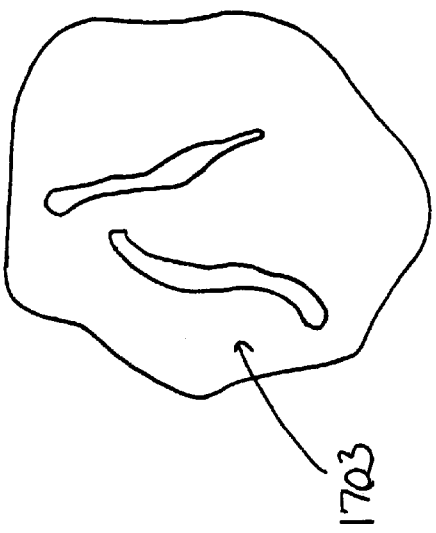
FIG. 17C is a top view of a lesion pattern.
Figure 17D:
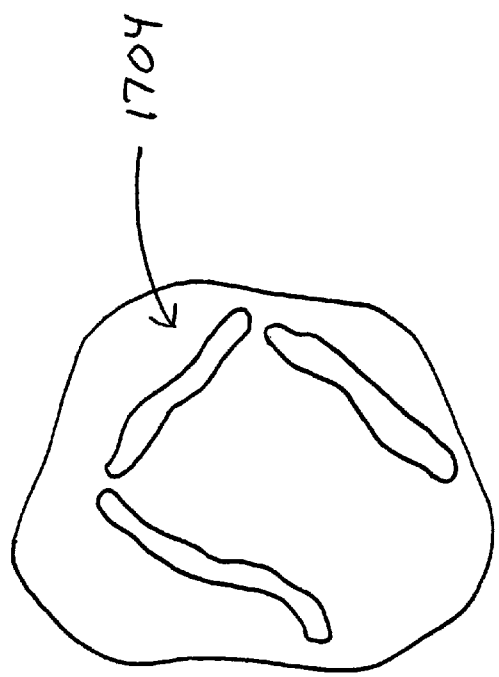
FIG. 17D is a top view of a lesion pattern.

It should be apparent from the previous figures, the element array, as well as the number, shape, and configuration of the energy emitting elements and temperature sensing elements can vary widely. This allows for the ablation tool to produce lesions of many different shapes and sizes for many types of procedures requiring body tissue ablation. For example, the energy emitting elements 630 of FIG. 6 would produce a lesion 1701 as approximately shown in FIG. 17A. The energy emitting elements 130, 230, 330, 730, 930, 1030, 1230, 1330, and 1430 in FIGS. 1–3, 7, 9, 10, 12–14 respectively may be used to produce the lesion 1702 as approximately shown in FIG. 17B. Similarly, the energy emitting elements 130, 230, 330, 1030, 1230, 1330, and 1430 in FIGS. 1–3, 10, 12–14 respectively may be used to produce the lesion 1703 as approximately shown in FIG. 17C. And, the energy emitting elements 130, 230, 330, 430, 530, 730, 830, 930, 1030, 1130, 1230, 1330, and 1430 in FIGS. 1–5, 7–13 respectively may be used to produce the lesion 1704 as approximately shown in FIG. 17D. The type and duration of the energy source will determine the final shape and size of the lesion.

Operation and use of an embodiment of an ablation tool can now be briefly described as follows. This example is not intended to be exclusive or limiting and the scope of the invention is provided by the attached claims and their equivalents. Let it be assumed that it is desired to introduce radio frequency energy (or any other ablative energy, such as microwave, ultrasound, light, and cryogenics, among others) into the tissue forming a chamber of the heart to cause ablation of the myocardium. Also let it be assumed that the tool is introduced into the chamber of the heart in a human being in a conventional open heart procedure. By using operator experience and preference, the tool is bent and formed into a desired shape to allow convenient assess to the ablation site by the element array and to produce a lesion of the desired shape. The element array is pressed against the tissue such that the energy emitting elements and temperature sensing elements are touching the tissue. Radio frequency is applied to the energy emitting elements which ablate the tissue. The temperature sensing elements (such as thermistors or thermocouples) measure the temperature of the energy emitting element and/or the element array. Fluid flows from the fluid source through the fluid lumen of the elongate member and element array and out the orifices in the element array effectively cooling the surrounding tissue to minimize collateral tissue damage.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. An ablation tool for forming lesions in body tissue of a subject at a desired ablation site, comprising:

an elongate member having a distal and proximal end;

an element array disposed on the elongate member distal end, wherein said element array has two free ends;

at least one energy emitting element disposed on the element array; and a source of energy coupled to the at least one energy emitting element, said source of energy capable of energizing the at least one energy emitting element to form a lesion in body tissue that is pressed against the at least one energy emitting element, wherein the elongate member and element array are sized and configured for nontransluminal placement of the at least one energy emitting element at a target site, and wherein at least one of the elongate member and element array are malleable such that they can take on a desired shape prior to positioning in the subject and substantially retain that shape as said element array is positioned in the subject at the desired ablation site, the desired shape selected so as to impart a desired lesion pattern on the body tissue at the ablation site.

2. The tool according to claim 1, wherein the ablation tool is adapted to treat cardiac tissue, wherein the element array further comprises at least one temperature sensing element, and wherein the ablation tool further comprises a fluid delivery path extending through the elongate member and the element array so as to be able to direct fluid from the ablation tool to the ablation site during operation.

3. The tool according to claim 2, wherein the at least one energy emitting element further comprises an electrically conductive material capable of emitting radio frequency energy, and said source of energy is capable of producing radio frequency energy.

4. The tool according to claim 1, wherein the element array further comprises a planar surface, said at least one energy emitting element disposed on said planar surface, whereby the pressing of said planar surface against body tissue also presses at least one energy emitting element against body tissue.

5. The tool according to claim 4 wherein the at least one energy emitting element has a shape which produces circular lesions.

6. The tool according to claim 4 wherein the at least one energy emitting element has a shape which produces a plurality of elongated lesions.

7. The tool according to claim 4 wherein the element array is elongated, and the at least one energy emitting element is disposed on the element array whereby an elongated lesion is formed by the pressing of said element array against body tissue.

8. The tool according to claim 7 wherein the element array is curved, and the at least one energy emitting element is disposed on the element array whereby a curved lesion is formed by the pressing of said element array against body tissue.

9. The tool according to claim 1 wherein the elongate member is made from a malleable material, and wherein the elongate member is adapted to be bent to allow easier positioning of the element array against body tissue.

10. The tool according to claim 1 wherein the element array has the shape of an elongated cylindrical rod which is attached to the elongate member distal end so that it extends in a substantially perpendicular direction relative to the elongate member and having a diameter defining a surface, and the at least one energy emitting element disposed on the element array, thereby pressing the element array against body tissue also presses the at least one energy emitting element against body tissue.

11. The tool according to claim 10 wherein the at least one energy emitting element is a band element disposed around the element array diameter on the surface.

12. The tool according to claim 10 wherein the element array is malleable, whereby the element array is adapted to be bent into a complex shape to allow for producing lesions of complex shape when the element array is pressed against body tissue.

13. The tool according to claim 12 wherein the elongate member is malleable, whereby the elongate member is adapted to be bent to allow easier positioning of the element array against body tissue.

14. A tool according to claim 1, wherein the element array comprises a block body.

15. A tool according to claim 14, wherein the element array block body is contiguous, and wherein said ablation tool comprises at least one fluid channel formed therein.

16. A tool according to claim 14, wherein the at least one energy emitting element is a plurality of discrete elements positioned to reside in the block body such that they define an exposed portion of a bottom surface.

17. A tool according to claim 1, wherein the element array transversely extends off a distal end portion of the elongate member.

18. A tool according to claim 1, further comprising a plurality of orifices located adjacent active elements on the element array adapted for dispensing fluid therefrom.

19. A tool according to claim 18, wherein the at least one element array is two, and wherein the ablation tool is adapted to simultaneously activate the energy emitting elements thereon so as to concurrently impart lesions onto the body tissue at the ablation site.

20. A tool according to claim 1, wherein the ablation tool is configured to provide a discontinuous arcuate shaped lesion pattern.

21. A tool according to claim 1, wherein the ablation tool is configured to provide a "U" shaped lesion pattern.

22. A tool according to claim 20, wherein the ablation tool is configured to provide at least two side by side elongated linear lesions.

23. A tool according to claim 1, wherein the ablation tool is configured to provide three substantially linear elongated lesions.

24. A tool according to claim 1, wherein the ablation tool is configured to provide an L shaped lesion.

25. A tool according to claim 24, wherein the L shaped lesion is substantially continuous.

26. An ablation tool for forming lesions in body tissue of a subject at a desired ablation site, comprising:
an elongate member having a distal and proximal end;
an element array disposed on the elongate member distal end; at least one energy emitting element disposed on the element array; and
a source of energy coupled to the at least one energy emitting element, said source of energy capable of energizing the at least one energy emitting element to form a lesion in body tissue that is pressed against the at least one energy emitting element, wherein the element array further comprises a planar surface, said at least one energy emitting element disposed on said planar surface, whereby the pressing of said planar surface against body tissue also presses at least one energy emitting element against body tissue, wherein the element array is elongated, and the at least one energy emitting element is disposed on the element array whereby an elongated lesion is formed by the pressing of said element array against body tissue, and wherein the element array is "L-shaped", and the at least one energy emitting element is disposed on the element array whereby an "L-shaped" lesion is formed by the pressing of said element array against body tissue.

27. An ablation tool for forming lesions in body tissue of a subject at a desired ablation site, comprising:
an elongate member having a distal and proximal end;
an element array disposed on the elongate member distal end;
at least one energy emitting element disposed on the element array; and
a source of energy coupled to the at least one energy emitting element, said source of energy capable of energizing the at least one energy emitting element to form a lesion in body tissue that is pressed against the at least one energy emitting element, wherein the element array further comprises a planar surface, said at least one energy emitting element disposed on said planar surface, whereby the pressing of said planar surface against body tissue also presses at least one energy emitting element against body tissue, wherein the element array is elongated, and the at least one energy emitting element is disposed on the element array whereby an elongated lesion is formed by the pressing of said element array against body tissue, and wherein the element array is "U-shaped", and the at least one energy emitting element is disposed on the element array whereby a "U-shaped" lesion is formed by the pressing of said element array against body tissue.

28. A non-transluminal ablation tool for delivering ablation treatment forming lesions in body tissue of a subject, comprising:
at least two malleable elongate members each having a distal and proximal end, the elongate members being joined together near the proximal ends and being spatially separated at the distal ends, wherein said elongate members are malleable so as to be able to take on a desired shape prior to positioning in the subject and so as to substantially retain the desired shape during positioning into the body of the subject, the desired shape corresponding to a desired lesion pattern to be imparted in the body tissue during the ablation treatment;
an element array disposed on each elongate member distal end;
at least one energy emitting element disposed on each element array; and
a source of energy coupled to each of the at least one energy emitting element, said source of energy capable of energizing each at least one energy emitting element, whereby the at least two malleable elongate members are bent in such a way as to provide simultaneous body tissue contact by each element array and therefore contact by each of the at least one energy emitting element to form at least one lesion in body tissue.

29. A non-transluminal ablation tool for forming lesions in body tissue of a subject, comprising:
an elongate member having opposing distal and proximal ends and a lumen extending therebetween;
an element array disposed on the elongate member distal end, the array further comprising at least one internal lumen and at least one orifice, the at least one internal lumen in fluid communication with elongate member lumen and terminating at the at least one orifice, wherein the elongate member terminates into the element array, and wherein the element array comprises a block body with opposing top and bottom surfaces, and wherein the element array is non-collapsible and is configured to substantially present its operative configuration prior to positioning in the subject;

at least one energy-emitting element disposed on the element array such that it resides on at least one of the top or bottom surfaces;

a source of energy coupled to the at least one energy emitting element, said source of energy capable of energizing the at least one energy emitting element to form a lesion in body tissue that is pressed against the at least one energy emitting element; and a fluid source coupled to the elongate member lumen, whereby fluid travels from the fluid source through the elongate member lumen and at least one array lumen and exiting through the at least one orifice bathing the surrounding body tissue with fluid, cooling the same.

30. The tool according to claim 29, wherein the element array is pivotally mounted to the elongate member distal end, wherein the element array transversely extends from the distal end of the elongate member, and wherein a plurality of emitting elements are positioned on the bottom surface of the block body.

31. A method for ablating body tissue comprising the steps of:

providing a non-transluminal ablation tool having at least two elongate members, the elongate members having a distal and proximal end, an element array disposed on each elongate member distal end such that the element array transversely extends therefrom, at least one radio frequency energy emitting element disposed on each element array, and a source of radio frequency energy coupled to the at least one energy emitting element, wherein the element arrays on the distal ends of the elongate members are spaced apart from each other, positioning the ablation tool such that each element array and the at least one energy emitting element are pressed against body tissue, and conveying radio frequency energy to the at least one energy emitting element for transmission into body tissue to form a lesion due to a heating effect.

32. A method for ablating body tissue comprising the steps of:

exposing target tissue of the patient's heart using conventional open heart procedures, providing an ablation tool having at least two malleable elongate members, the elongate members having a distal and proximal end and a lumen between the distal and proximal ends, a malleable element array disposed on each elongate member distal end, the array further comprising at least one internal lumen and at least one orifice, the at least one internal lumen in fluid communication with a selected one of the elongate member lumens and terminating at the at least one orifice, at least one radio frequency energy emitting element disposed on each element array, a source of radio frequency energy coupled to the at least one energy emitting element, and a fluid source coupled to the elongate member lumens, bending and forming at least one of the elongate members and associated element array into a desired shape corresponding to the shape of a lesion to be formed onto the target tissue of the patient's heart at a desired ablation site, positioning the ablation tool such that at least one of the energy emitting elements of each of the arrays is pressed against and in contact with body tissue at the desired ablation site, initiating fluid flow from the fluid source so that the fluid travels through the elongate member lumens, into the at least one lumen of each array, and out through the at least one orifice in each array so as to bathe the body tissue surrounding the ablation site with fluid to cool the surrounding tissue to inhibit collateral tissue damage, conveying radio frequency energy to at least one of the at least one energy emitting element of each array for transmission into body tissue to form a lesion due to a heating effect, terminating the supply of radio frequency energy after a time sufficient to produce the desired lesion in the body tissue at the ablation site, terminating the flow of fluid, and withdrawing the ablation tool from the patient.

* * * * *

UNITED STATES PATENT AND TRADEMARK OFFICE
CERTIFICATE OF CORRECTION

PATENT NO.     : 6,290,699 B1
DATED          : September 18, 2001
INVENTOR(S)    : Hall et al.

It is certified that error appears in the above-identified patent and that said Letters Patent is hereby corrected as shown below:

Column 9,
Lines 52 and 53, should be changed to appear as follows:
-- end;
      at least one energy emitting element disposed on the element array; and --

Signed and Sealed this

Seventh Day of January, 2003

JAMES E. ROGAN
*Director of the United States Patent and Trademark Office*